United States Patent [19]
Groffen et al.

[11] Patent Number: 5,667,981
[45] Date of Patent: Sep. 16, 1997

[54] DIAGNOSTICS AND TREATMENTS FOR CANCERS EXPRESSING TYROSINE PHOSPHORYLATED CRKL PROTEIN

[75] Inventors: John H. Groffen; Nora C. Heisterkamp; Johanna Ten Hoeve, all of Los Angeles, Calif.

[73] Assignee: Childrens Hospital of Los Angeles, Los Angeles, Calif.

[21] Appl. No.: 242,513

[22] Filed: May 13, 1994

[51] Int. Cl.$^6$ .................... G01N 33/574; G01N 33/53
[52] U.S. Cl. .................. 435/7.23; 435/7.24; 436/63; 436/64; 436/813
[58] Field of Search .................... 435/7.23, 7.24; 436/63, 64, 813

[56] References Cited

U.S. PATENT DOCUMENTS 5,352,660  10/1994  Pawson ........................... 514/12

FOREIGN PATENT DOCUMENTS

| | | |
|---|---|---|
| 2 054 602 | 5/1993 | Canada . |
| 63-218629 | 9/1988 | Japan . |
| WO-A-93 03377 | 2/1993 | WIPO . |

OTHER PUBLICATIONS

Huhn, et al., *PNAS*, vol. 84, No. 13, pp. 4408–4412, 1987.
Nichols, et al., *Blood*, vol. 84, No. 9, pp. 2912–2918, Nov. 1994.
Ten Hoeve, et al., *Blood*, vol. 84, No. 6, pp. 1731–1736, Sep. 1994.
Oda, et al., *J. Biol. Chem.*, vol. 269, No. 37, Sep. 1994, pp. 22925–22928.
Ten Hoeve, et al., *Oncogene*, vol. 8, No. 9, pp. 2469–2474, Sep. 1993.
Koch, C.A., et al., "SH2 and SH3 domains: elements that control interactions of cytoplasmic signaling proteins", *Science*, 252: 668–74 (1991).
Mayer, B.J., et al., "A novel viral oncogene with structural similarity to phospholipase C", *Nature*, 332: 272–275 (1988).
Mayer, B.J. and Hanafusa, H., "Mutagenic analysis of the v–crk oncogene: requirement for SH2 and SH3 domains and correlation between increased cellular phosphotyrosine and transformation", *J. Virol.*, 64: 3581–3589 (1990).
Reichman, C.T., et al., "The product of the cellular crk gene consists primarily of SH2 and SH3 regions", *Cell Growth Differ.*, 3: 451–460 (1992).
Freed, E. and Hunter, T., "A 41–kilodalton protein is a potential substrate for the p210$^{bcr-abl}$ protein–tyrosine kinase in chronic myelogenous leukemia cells", *Mol. Cell. Biol.*, 12: 1312–1323 (1992).
Naldini, L., et al., "Phosphotyrosine antibodies identify the p210$^{c-abl}$ tyrosine kinase and proteins phosphorylated on tyrosine in human chronic myelogenous leukemia cells", *Mol. Cell. Biol.*, 6: 1803–1811 (1986).

ten Hoeve, J., et al., "Isolation of NotI sites from chromosome 22q11", *Genomics*, 18: 588–597 (1993).
Fioretos, T., et al., "CRK proto–oncogene maps to human chromosome band 17p13", *Oncogene*, 8: 2853–2855 (1993).
Matsuda, M., et al., "Two species of human CRK cDNA encode proteins with distinct biological activities", *Mol. Cell Biol.*, 12:3482 (1992).
ten Hoeve J., et al., "Cellular interactions of CRKL, an SH2–SH3 adaptor protein", *Cancer Res.*, 54 (10): 2563–2567 (May 15, 1994).
Feller, S.M., et al., "c–Abl kinase regulates the protein binding activity of c–crk" *EMBO J*, 13 (10): 2341–2351 (May 15, 1994).
Tanaka, S., et al., "Both the SH2 and SH3 domains of human CRK protein are required for neuronal differentiation of PC12 cells", *Mol. Cell Biol.*, 13:4409 (1993).
Blake, T.J. and Langdon, W.Y., "A rearrangement of the c–cbl proto–oncogene in HVT 78–T lymphoma cells results in a truncated protein", *Oncogene* 7: 757–762 (1992).
Blake, T.J., et al., "The truncation that generated the v–cbl oncogene reveals an ability for nuclear transport, DNA binding and acute transformation", *EMBO J*, 12 (5) 2017–2026 (1993).
Langdon, W.Y., et al., "v–cbl, an oncogene from a dual–recombinant murine retrovirus that induces early B–lineage lymphomas", *Proc. Natl. Acad. Sci.*, 86: 1168–1172 (1989).
Andoniou, C.E., et al., "Tumour induction by activated abl involves tyrosine phosphorylation of the product of the cbl oncogene", *EMBO J*, 13 (19) 4515–4523 (Oct. 1994).
Blake, T.J., et al., "The sequences of the human and mouse c–cbl proto–oncogenes show v–cbl was generated by a large truncation encompassing a proline–rich domain and a leucine zipper–like motif", *Oncogene*, 6: 653–657 (1991).
Donovan, J.A., et al., "The Protein Product of the c–cbl Protooncogene Is the 120–kDa Tyrosine–phosphorylated Protein in Jurkat Cells Activated via the T Cell Antigen Receptor", *J. Biol. Chem.*, 269 (37), 22921–22924 (Sep. 1994).
Odai, H., et al., "The Proto–oncogene Product c–Cbl Becomes Tyrosine Phosphorylated by Stimulation with GM–CSF or Epo and Constitutively Binds to the SH3 Domain of Grb2/Ash in Human Hematopoietic Cells", *J. Biol. Chem.*, 270 (18), 10800–10805 (1995).

*Primary Examiner*—Toni R. Scheiner
*Attorney, Agent, or Firm*—Morgan & Finnegan, L.L.

[57] ABSTRACT

The invention relates to methods and kits for diagnosing cancers arising from cells which express tyrosine phosphorylated CRKL protein, such as cells having the Philadelphia (Ph) chromosome, which includes chronic myelogenous leukemia (CML) and acute lymphoblastic leukemia (ALL), through the detection of increased levels of phosphorylated CRKL protein or through the detection of increased CRKL gene copy or mRNA expression. The invention also relates to methods of treating such cancers.

20 Claims, 7 Drawing Sheets

DIAGNOSTICS AND TREATMENTS FOR CANCERS EXPRESSING TYROSINE PHOSPHORYLATED CRKL PROTEIN

This invention was made with United States Government support under National Cancer Institute Grant No. CA 47456. The United States Government has certain rights in this invention.

I. TECHNICAL FIELD

The invention relates to methods and kits for diagnosing cancers arising from cells which express tyrosine phosphorylated CRKL protein, such as cells having the Philadelphia (Ph) chromosome, which includes chronic myelogenous leukemia (CML) and acute lymphoblastic leukemia (ALL), through the detection of increased levels of phosphorylated CRKL protein or through the detection of increased CRKL gene copy or mRNA expression. The invention also relates to methods of treating such cancers.

II. BACKGROUND ART

Chronic myelogenous leukemia (CML) and Ph-positive acute lymphoblastic leukemia (ALL) are characterized by a specific chromosomal translocation, the t(9;22) leading to the formation of the Philadelphia (Ph) chromosome. The ABL proto-oncogene from chromosome 9 is juxtaposed to the BCR gene on chromosome 22 by this translocation. The chimeric BCR/ABL gene produces P210 or P190 fusion proteins (reviewed in 1–3, 29, 30). The ABL protein is a tyrosine-specific protein kinase of the non-receptor type, and its tyrosine kinase activity is deregulated in BCR/ABL as a consequence of the attachment of the BCR moiety (31, 32). Specifically, ABL encodes a P145 non-receptor protein tyrosine kinase (PTK), and contains several other functional domains, including an SH3, an SH2 and an F-actin binding domain (reviewed in 4). Likewise, the BCR protein is multifunctional: the domain encoded by BCR exon-1 has serine/threonine kinase activity, can dimerize and binds the ABL SH2 domain in a non-phosphotyrosine-dependent manner (1, 5); the central part of the molecule has homology to GTP exchange factors (6); and its carboxy terminus has GTPase-activating protein (GAP) activity towards small $p21^{ras}$-like molecules, including $p21^{rac}$(7). Both BCR and ABL are thus implicated in signal transduction. The BCR/ABL p210 contains the BCR exon 1 encoded domain, the exchange factor homology domain and the majority of the ABL protein, and the oncogenic effect of BCR/ABL must be related to the perturbation of the normal BCR and/or ABL signaling pathways.

Aspects of a signaling cascade involving the EGF-receptor, a receptor protein tyrosine kinase, have recently been elucidated. Upon ligand binding, the EGF-receptor is auto-phosphorylated on tyrosine, thereby providing a binding site for GRB2. GRB2, which consists of a single SH2 domain flanked by two SH3 domains, associates with tyrosine phosphorylated proteins through its SH2 domain and with the RAS guanidine-nucleotide exchange factor mSOS1 through its SH3 domains (8; and reviewed in 9). Thus recruited to the plasma membrane, mSOS1 can activate $p21^{ras}$. Recently, it has been demonstrated that GRB2 also binds BCR/ABL via $Y^{177}$, a tyrosine residue encoded by BCR exon 1 only phosphorylated in BCR/ABL expressing cells (10, 11).

Through the use of experimental animal models, it has been shown that the BCR/ABL protein is sufficient to cause leukemia (33–35). Currently, the mechanism by which this takes place is largely unknown. BCR/ABL has been found in association with an increasing number of other proteins. A protein called ph-P53 complexes with BCR/ABL in the CML cell line K562 (36–37). The BCR protein itself is phosphorylated by and found in complex with BCR/ABL in K562 and transfected COS cells (37–39). Tyrosine-phosphorylated rasGAP, its associated proteins p190 and p62 and the adaptor proteins GRB-2 and SHC are also co-immunoprecipitated with BCR/ABL (10, 11, 40, 41). GRB-2 is constitutively associated with the $p21^{ras}$ nucleotide exchange factor SOS via its SH3 domains, and BCR/ABL might therefore intervene with normal cellular signaling by upregulating $p21^{ras}$ activity (10, 43). Increased tyrosine phosphorylation of a hematopoietic cell lineage specific tyrosine kinase, $p93^{c-fes}$, has also been reported (44).

Several other "adaptor proteins" have been identified to date (12). CRK was initially discovered as the oncogene v-crk (13). CRK consists of an amino terminal SH2 domain and two tandem SH3 domains. Deletion of the carboxy terminal SH3 domain leads to transformation which is accompanied by an increase in cellular phosphotyrosine (14, 15, 28). A gene, CRKL, encoding a protein with a 60% overall homology to CRK, was recently isolated (16, 28). The CRKL gene was fortuitously identified through its location centromeric to the BCR gene on human chromosome 22 (26). CRKL consists solely of an SH2 domain and two tandem SH3 domains in the absence of a catalytic domain (16).

Presently CML and ALL patients are treated chemotherapeutically with conventional therapeutics and radiation. Such treatment is plagued by well-known side-effects and is often of limited effect. No effective treatment for these leukemias is known. Thus, other compositions and methods for treating such cancers are being sought.

There remains a need in the art for effective therapeutic compositions and methods to treat leukemia or ameliorate its effect on a human patient.

III. SUMMARY OF THE INVENTION

This invention relates to methods and kits for diagnosing cancers arising from cells which express tyrosine phosphorylated CRKL protein. Such cells include those having the Philadelphia (Ph) chromosome, which includes chronic myelogenous leukemia (CML) and acute lymphoblastic leukemia (ALL). Diagnosis is accomplished by detecting increased levels of phosphorylated CRKL protein or through the detection of increased CRKL gene copy or mRNA expression. The invention also relates to methods of treating such cancers and compositions for such treatment.

One aspect of the invention involves measuring the amount of phosphorylated CRKL and non-phosphorylated CRKL protein in cells suspected of expressing increased levels of CRKL and determining the ratio of phosphorylated CRKL to non-phosphorylated CRKL. In this method, when only cells suspected of expressing increased levels of CRKL are tested, then any ratio above background may be considered as indicative of cancer. Usually a ratio of about 5% phosphorylated to non-phosphorylated CRKL or above is associated with the presence of cancer. When normal cells are used as a control, the ratio of phosphorylated to non-phosphorylated CRKL is elevated in cells associated with the presence of cancer, but not in normal cells. Normal cells may be obtained from another individual or may be known non-neoplastic cells obtained from the individual being tested.

Another aspect of the invention involves the treatment of cancer arising from cells which express tyrosine phosphorylated CRKL protein in mammals, particularly humans.

The present invention provides a method of diagnosing cancers arising from cells which express a tyrosine phosphorylated CRKL protein. The method of the invention comprises obtaining a sample of cells suspected of expressing tyrosine phosphorylated CRKL protein and determing the percent increase in tyrosine phosphorylated CRKL protein relative to normal control cells. The increase in the expression of phosphorylated CRKL protein relative to controls is associated with the presence of cancer.

The method of the invention is particularly useful for diagnosing cancers which arise from the Philadelphia chromosome. Such cancers include chronic myelogenous lukemia (CML) and acute lymphoblastic lukemia (ALL).

Various methods may be used to detect the presence of the tyrosine phosphorylated CRKL protein. According to one embodiment of the invention the CRKL protein is detected immunologically, for example, with an antiphosphortyrosine antibody. The binding of antibodies specific for CRKL protein may be detected using a variety of methods including colorimetric and radioimmunoassays.

This invention also provides kits for diagnosing the cancers arising from cells expressing tyrosine phosphorylated CRKL protein. Such kits comprise a reagent capable of specifically binding to tyrosine phosphorylated CRKL protein. The binding of this reagent could then be detected directly or indirectly depending upon whether the reagent is itself labeled with a detectable marker or reacts with a second reagent which contains a detectable marker. The kit further comprises instructions for using the reagent in an assay to detect the presence of tyrosine phosphorylated CRKL protein and for correlating the presence of that protein with cancer. Other forms of the kit may further comprise buffer reagents and reaction vessels to accomplish the assays necessary for detecting the CRKL protein. Another component which may be present in the kit is a control reagent which comprises CRKL protein obtained from non-neoplastic cells. This control reagent may be used as a reference for determining the percent increase of tyrosine phosphorylated CRKL protein. The reagent for specifically binding to tyrosine phosphorylated CRKL protein preferably comprises an antibody. A second antibody capable of detecting the CRKL specific protein may also be a component of the kit. The second antibody may be labeled with a detectable marker such as an enzyme, a radioisotope, fluorescent or bioluminesent moiety. In a preferred embodiment of the invention, the enzyme is horseradish peroxidase. The kit of the invention is particularly well suited for being adapted to use with Western blot analysis.

Another embodiment of this invention is a method of treating individuals with cancers arising from cells which express tyrosine phosphorylated CRKL protein. The method of the invention comprises administering a therapeuticly effective amount of at least one composition which inhibits the synthesis or the activity of CRKL protein. Inhibition of the synthesis of CRKL protein may be accomplished in a variety of methods including inhibition of transcription, translation or protein activity. Inhibition of transcription may be accomplished by causing the formation of triple helices through the use of oligonucleotides. Such methods include inhibiting mRNA translation by complementary antisense RNA or DNA. Destruction of mRNA by antisense RNA coupled with ribozymes also may be used to prevent synthesis of CRKL protein. Synthesis of CRKL protein may also be inhibited by interfering with mRNA using RNA sequences amologous to a portion of the mRNA which represents an important regulatory sequence.

RNA or DNA useful for inhibiting CRKL synthesis may be administered to individuals in the treatment using a variety of methods including infection with a vector, for example, a viral vector, capable of infecting cancer cells, or through use of one or more types of carriers including liposomes, lipid base carriers, and lipid complexes.

Another method of inhibiting the neoplastic activity of CRKL protein is to inhibit the action of the protein itself. Accordingly, the invention includes methods of treating individuals by inhibiting the phosphorylation of CRKL protein. Inhibition of phosphorylation may be accomplished by methods which inhibit the enzymatic phosphorylation of CRKL protein or which compete with CRKL protein in the phosphorylation reaction. In one embodiment of the invention a polypeptide comprising an amino acid sequence which competes with CRKL protein for phosphorylation is administered to the individual. In a preferred embodiment, this polypeptide would be a fragment of a CRKL protein itself. In a particularly preferred embodiment, this fragment would comprise a region of amino acids 193-210 of CRKL protein. Without being bound by theory, it is believed that one or more of the two tyrosine residues in this region are particularly relevant to the neoplastic activity of the phosphorylated CRKL protein. In particular, phosphorylation of the tyrosine in the sequence AYA may be particularly relevant to the neoplastic activity.

This invention also includes pharmaceutical compositions for treating individuals with cancers arising from cells which express a tryosine phosphorylated CRKL protein. Such compositions comprise at least one component which inhibits synthesis of the activity of CRKL protein and a pharmaceutical acceptable carrier. Such carriers may include physiologically acceptable buffers, for example, saline or phosphate buffered saline. The pharmaceutical compositions may comprise one or more components which inhibit the synthesis of CRKL protein and/or its activity. Such components would be the same as those described above which are useful for the method of treating persons with cancer arising from phosphorylated CRKL protein.

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

IV. BRIEF DESCRIPTION OF THE DRAWINGS

FIG. 2. Identification of CRKL protein. Panel A shows the segments of CRKL against which the antisera were raised. The relative locations of the SH2 and SH3 domains are as indicated. Panel B shows a Western blot analysis of CRKL expression. Cellular extracts include those of the human myelogenous leukemia cell line K562 (K); the human kidney carcinoma cell line A498 (A); COS-1 cells (−) and COS-1 cells transfected with CRKL (+). The location of 43 and 29 kDa standards is shown to the left. The arrow indicates the position of the group of P38 proteins. Antisera used are indicated beneath each panel.

FIG. 3. CRKL is phosphorylated on tyrosine in cells expressing ABL and BCR/ABL. Panel A shows analysis of the CML cell line K562. Antisera used for immunoprecipitation are shown above the lanes and those for Western blot analysis below each panel. Lanes 1 contain total cellular extracts. NRS=non-related rabbit serum. The prominent band around 50 kDa is immunoglobulin. Panel B. Western blot analysis of co-transfections with CRKL, BCR/ABL and ABL in COS-1 cells. Antisera used are shown to the left. Extracts include those of K562 (lane 1) and COS-1 cells (lane 2); and of COS-1 cells transfected with CRKL, BCR/ABL P210+CRKL, BCR/ABL P210, CRKL+ABL, and ABL (lanes 3–7, respectively). The location of BCR/ABL P210, ABL P145 and CRKL P38 is shown to the right. Panel C. P38 consists of closely migrating forms. Lanes 1 and 2, K562 extracts probed with CH15 and CH16, respectively. Lanes 3 and 4, extracts of COS-1 cells transfected with CRKL+ABL and with CRKL alone, probed with CH16. Lanes 5 and 6, the K562 and CRKL+ABL extracts (lanes 2 and 3) reprobed with α-p-Tyr (OSI) antibodies.

FIG. 4. Western blot analysis of CH15 and CH16 immunoprecipitates from transfected COS-1 cells. A–C. Co-immunoprecipitation of ABL and BCR/ABL with CRKL antisera. The same Western blot was subsequently used with the antisera indicated to the left. The transfected COS-1 cell extracts used are indicated at the top of the figure. Lanes 1,3,5 and 7 contain total cellular extracts; lanes 2,4,6 and 8 contain CH15 immunoprecipitates; lane 9 a CH16 immunoprecipitate; lane 10 an immunoprecipitate with CH15 pre-immune serum (panels A and B only). Lanes containing immunoprecipitates are characterized by the prominent immunoglobulin band at around 50 kDa. The locations of P145, P210 and P38 are indicated to the right. D. The tyrosine kinase FER does not co-immunoprecipitate with CRKL. Extracts of COS-1 cells cotransfected with CRKL+FER were loaded directly (left lanes) or after immunoprecipitation with CH15 (right lanes). Antisera used for Western blotting are indicated beneath each panel. The locations of P94$^{fer}$ and P38$^{crkl}$ are as indicated.

FIG. 5. Binding of CRKL to cellular proteins. A. Western blot-binding assay using GST-CRKL. Western blots containing extracts of COS-1 cells transfected with ABL were incubated with GST, with the GST-CRKL fusion protein, or with α-ABL or α-SOS-1 antibodies as indicated below each lane. B. Co-immunoprecipitation of CRKL and P170$^{SOS}$ from K562 extracts. Lane 1 contains a total cellular extract. Lanes 2 and 3 contain the indicated immunoprecipitates. The top part of the membrane was incubated with α-SOS antibodies, the bottom part with the CH16 antiserum.

FIG. 8. The presence of BCR/ABL correlates with CRKL phosphorylation. Panel A, samples of Ph-negative and Ph-positive ALL patients and of two CML blast crisis patients. Panel B, peripheral blood samples of Ph-negative patients including a normal control (S15), AML (S72), diffuse large cell lymphoma (S73,S74), myeloproliferative syndrome (S90), Down's syndrome (S232), CLL (S246) and CMML (S336). Blots were probed with CRKL antiserum CH16.

V. DETAILED DESCRIPTION OF THE INVENTION

The invention relates to methods and kits for diagnosing cancers arising from cells which express tyrosine phosphorylated CRKL protein. Such cells include those having the Philadelphia (Ph) chromosome, including chronic myelogenous leukemia (CML) and acute lymphoblastic leukemia (ALL) cells. Diagnosis is achieved through the detection of increased levels of phosphorylated CRKL protein or through the detection of increased CRKL gene copy or mRNA expression. The invention also relates to methods of treating such cancers.

Example 1 infra, demonstrates the CRKL protein product is a 38-kDa protein expressed in a variety of cell types. The data presented show that P38 is phosphorylated on tyrosine by ABL and BCR/ABL, and demonstrate that it forms complexes in vivo with both ABL and BCR/ABL. In addition, CRKL is capable of binding to mSOS1. These data provide evidence that CRKL is part of a signal transduction pathway involving ABL, and show one mechanism through which BCR/ABL might exert its oncogenic effect.

We have recently demonstrated that the adaptor protein CRKL is phosphorylated by ABL and BCR/ABL, and that CRKL is capable of forming specific complexes with ABL and BCR/ABL in COS-1 cells overexpressing these proteins. The hypothesis that CRKL would function as a substrate for BCR/ABL in vivo was strengthened by the finding that CRKL is prominently tyrosine-phosphorylated in the CML cell line K562 (45). This suggested that CRKL may play a role in mediating signals of the activated BCR/ABL oncoprotein in CML. Because of the increasing number of different proteins that already have been implicated in signal transduction of BCR/ABL using in vitro techniques and cell lines, the experiments set forth in Example 2 were conducted to establish in a more direct way whether CRKL could be involved in the development of CML. In that study, the data demonstrate that CRKL is clearly tyrosine-phosphorylated in peripheral blood cells of CML and Ph-positive ALL patients expressing the BCR/ABL protein, but not in BCR/ABL-negative peripheral blood cells. The level of CRKL phosphorylation correlates well with the level of BCR/ABL expression. These data demonstrate that tyrosine-phosphorylation of CRKL is a direct consequence of BCR/ABL expression. Accordingly, phosphorylation of CRKL may be used as a diagnostic indicator for BCR/ABL activity in Ph-positive leukemia.

The present invention represents an advance over the prior art in that it allows for the diagnosis of cancers arising from cells which express tyrosine phosphorylated CRKL, such as the cancers CML and ALL, by directly measuring the 38-KPO. CRKL protein as opposed to measuring the BCR/ABL P210 or P190 fusion proteins. The advantage is due to the comparative stability and protease resistance of the relatively small CRKL protein as opposed to the relatively large and unstable P210 or P190 fusion proteins. The nucleic acid and amino acid sequences of CRKL are described in ten Hoeve et al. *Oncogene*, 8: 2469–2474 (1993) which is incorporated herein by reference.

The methods of diagnosing cancers arising from cells expressing phosphorylated CRKL are based upon detecting the presence of phosphorylated CRKL in the cells of a cancer patient or a suspected cancer patient. The presence of an approximately 40 kDA phosphorylated CRKL compared to a 38 kDA non-phosphorylated CRKL is generally associated with the presence of cancer.

The first embodiment of the invention is based upon the discovery by the inventors that normal cells have either no or little detectable tyrosine phosphorylated CRKL (generally less than 2–4%). The first embodiment of the invention therefore involves diagnosing cancer by determining whether cells of the patient have an elevated level of tyrosine-phosphorylated CRKL. The presence of an elevated level of tyrosine-phosphorylated CRKL indicates that the patient has cancer.

In this embodiment of the invention, a suitable method of detecting non-phosphorylated and phosphorylated CRKL in the cells must be used. Any technique which can measure theses proteins in a cell can be used. Examples include Western blots or any type of immunoassay. Examples of the latter include various types of radioimmunoassays (RIA) or enzyme-linked immunosorbent assays (ELISA). When a Western blot or other similar assay is used only one antibody may be used to detect both the 38 kDA non-phosphorylated CRKL and the 40 kDA phosphorylated CRKL and their relative amounts may be compared. When either a Western blot or an immunoassay is used, a first antibody may be used to detect CRKL, whether phosphorylated or not, and a second antibody may be used to detect only the phospho-tyrosine residue on phosphorylated CRKL.

The methods of treating cancers arising from cells which express phosphorylated CRKL include methods for reducing the amount of CRKL protein and methods for blocking phosphorylation of CRKL. Methods for reducing the amount of CRKL protein include the use of antisense nucleotides or ribozymes to decrease or prevent transcription or translation of CRKL mRNA. For example, antisense nucleotides or ribozymes specific, i.e. complimentary, for mRNA encoding CRKL to decrease or prevent the translation of that mRNA into protein. It will be apparent from the above that nucleotides which form triple helices are also useful in the methods of the invention.

The antisense nucleotides and ribozymes may be in the form of oligonucleotide constructs or they may be encoded by a nucleotide construct, such as a retroviral vector. U.S. Pat. No. 5,246,921 of Reddy et al., which is herein incorporated by reference, describes the use of ribozymes to cleave bcr-abl mRNA and may accordingly be adapted to cleave CRKL mRNA. The antisense nucleotides or ribozymes, or DNA encoding them, may be delivered to the cells in any suitable manner, for example, in liposomes, lipid based carriers, or lipid based complexes. They may also be associated with a protein. This delivery may be done to the cells in vitro or in vivo. Methods described in U.S. Pat. No. 5,283,185 of Epand et al. which describes lipid carriers for transferring nucleic acids into cells may be used and is incorporated herein by reference.

Methods for blocking phosphorylation of CRKL include the use of synthetic peptides which compete with the region of CRKL which is phosphorylated. Preferably, if the synthetic peptide contains a region identical to the region of CRKL which is phosphorylated, then the synthetic peptide will not contain the regions necessary for transmitting the signal which is normally transmitted by phosphorylated CRKL. Without being bound by theory, it is believed that the portion of the CRKL amino acid sequence corresponding to residues 193 through 210 comprises one or more of the tyrosine residues associated with conferring the phosphorylated form of CRKL with neoplastic activity. In particular, the tyrosine residues in the sequences SYG and AYA and particularly AYA are believed to be associated with the proliferative activity of CRKL.

Accordingly, another alternative is that the peptide will be altered in the region which is analogous to the region of CRKL in which the tyrosine is phosphorylated.

The synthetic peptides may be delivered to the cells in any suitable manner, for example, in liposomes, lipid based carriers, or lipid based complexes. Alternatively, the peptide may be encoded by a nucleotide construct, such as a retroviral vector. This delivery may be done to the cells in vitro or in vivo.

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLE 1

Materials and Methods

Antisera

Antisera were prepared against GST fusion proteins containing two overlapping regions of the CRKL protein. For CH15 antiserum, an RsaI-RsaI CRKL cDNA fragment (encoding amino acid residues 128–247) was inserted into pGEX-2T (Pharmacia); for CH16 antiserum, a smaller Sau3A-RsaI CRKL cDNA fragment (encoding amino acid residues 184–247) was used. The resulting GST fusion proteins were purified on glutathione-Sepharose columns (Pharmacia) and used to immunize rabbits. Anti-p-Tyr (Ab-2), α-BCR (BCR Ab-2), and α-ABL (ABL Ab-3) monoclonal antibodies were from Oncogene Science, Inc. (OSI), the α-SOS polyclonal rabbit antiserum was from UBI. The RC-20 α-p-Tyr antibodies were from Transduction Laboratories. The rabbit polyclonal antiserum directed against the tyrosine kinase FER (CH6) has been previously described (17).

Expression in COS-1 cells

FER, ABL, BCR, BCR/ABL P210 and BCR/ABL P190 constructs for transient expression in COS-1 cells consisted of complete cDNAs inserted into a modified SV40 based mammalian expression vector, pCDX (18). The entire CRKL coding region was inserted into the eukaryotic expression vector pSG5 (Stratagene). Constructs were introduced into COS-1 cells using the DEAE-dextran method essentially as described (19). Cells were harvested 60–72 hrs after transfection.

Preparation of extracts and immunoprecipitations

Cells were suspended in 0.5 ml ice-cold lysis buffer (25 mM Na-phosphate pH 7.2, 150 mM NaCl, 1% Triton X-100, 5 mM EDTA, 50 mM NaF, 2 mM PMSF, 2 mM Na$_3$V$_4$, 20 µg/ml leupeptin, 20 µg/ml aprotinin) and left on ice for 15–45 minutes. Cells were further disrupted by passage through 18 and 25 g needles, and nuclei and debris were pelleted (30 min at 12,000×g, 4° C). COS-1 cell extracts or K562 cell extracts containing 250 or 500 µg of protein, respectively, were incubated for 90 min at 4° C. with 5 µl of antiserum; immune complexes were collected after an additional 30 minutes incubation with 5 µl protein A agarose beads (BRL), washed 4× with lysis buffer, and boiled in 1×SDS sample buffer prior to gel electrophoresis.

Western blotting and immunodetection

Proteins were transferred to Hybond-ECL (Amersham) using a mini trans-blot apparatus (Biorad). Membranes were blocked overnight at 4° C. in TBST (20 mM Tris-HCl, pH 8.0, 150 mM NaCl, 0.1% Tween)+5% non-fat milk (Biorad) and incubated for 2 hours at room temperature with the antisera; bound antibodies were detected with HRP-labeled secondary antibodies (Biorad). Membranes to be used with α-p-Tyr antibodies were blocked in TBST+2% BSA+1% ovalbumin. RC-20 was used according to the manufacturer's recommendations. Blots were developed using the ECL reagents (Amersham) and exposed to Hyperfilm-ECL (Amersham).

Blots were stripped for 30 minutes at 55° C. in 2% SDS, 100 mM β-mercaptoethanol, 62.5 mM Tris-HCl pH 6.8.

In the Western blot binding assay purified GST and GST-CRKL fusion proteins were used. The GST-CRKL fusion protein contains the entire CRKL coding region lacking only the first six N-terminal amino acids. Western blots were blocked for 1 hour in PBS+0.1% Tween+5% milk and incubated for 2 hours at room temperature with the GST or GST-CRKL proteins (at 1 or 2 µg/ml, respectively) in binding buffer (25 mM Na-phosphate buffer pH 7.2, 150 mM NaCl, 0.1% Tween 70, 2.5 mM EDTA, 20 mM NaF, 1% non-fat milk, 1 mM DTT, 10 µg/ml leupeptin and 10 µg/ml aprotinin). Bound GST proteins were detected by subsequent incubations with CH15 (which also contains antibodies against GST epitopes) and HRP-labeled secondary antibodies in binding buffer, and developed as described above.

Northern blot analysis

RNAs were isolated using guanidine-isothiocyanate (19). 15 µg of total RNA was run on a formaldehyde/agarose gel and blotted to nitrocellulose (20). Post-hybridization washes were performed in 0.3×SSC at 65° C.

Results

Expression of CRKL

Figure 1:
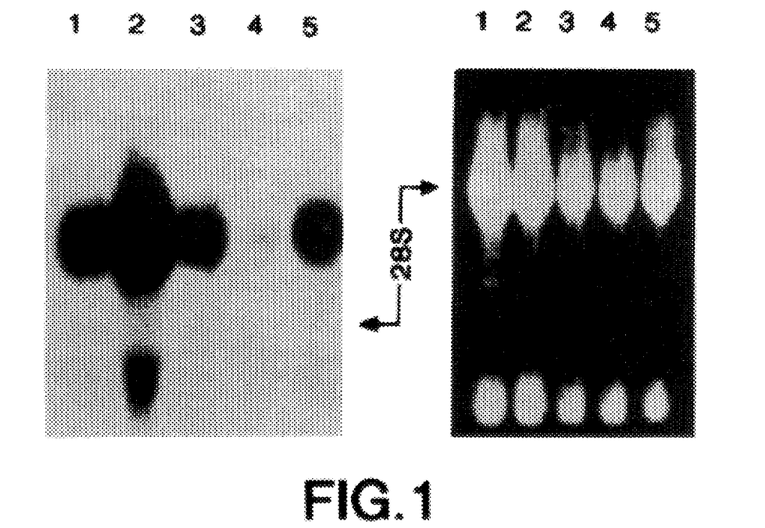
FIG. 1. Northern blot analysis of CRKL expression. Human RNAs are from the cell lines A498 (kidney carcinoma) lane 1; K562 (myelogenous leukemia) lane 2; CHAGO (bronchogenic carcinoma) lane 3; A172 (glioblastoma) lane 4 and HepG2 (hepatoma) lane 5. Panel A was hybridized to a human CRKL cDNA containing the entire coding region. The ethidium stained gel in panel B serves as a loading control.

Northern blot analysis on RNAs isolated from different mouse tissues showed that murine crkl, similar to c-crk in chicken (15) was ubiquitously expressed as a 6 kb mRNA in all tissues tested (not shown). Among human cell lines, CRKL is relatively abundantly expressed in the CML cell line K562 (FIG. 1 panel A, lane 2) and at a lower level in the hepatoma cell line HepG2 (lane 5). In contrast, CRK mRNA expression was higher in HepG2 than in K562 (not shown).

Figure 2A:
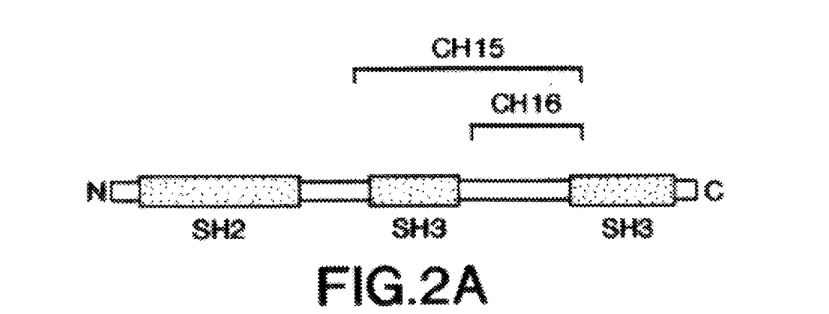

Two overlapping regions within the central domain of CRKL were expressed as GST fusion proteins in bacteria and used to raise antisera. CH15 is directed against the N-terminal SH3 domain and the region between the SH3 domains, whereas CH16 is raised against the latter junction region only (FIG. 2A). The junction region polypeptide of 64 amino acid residues is diverged considerably between CRK and CRKL (16)

Figure 2B:
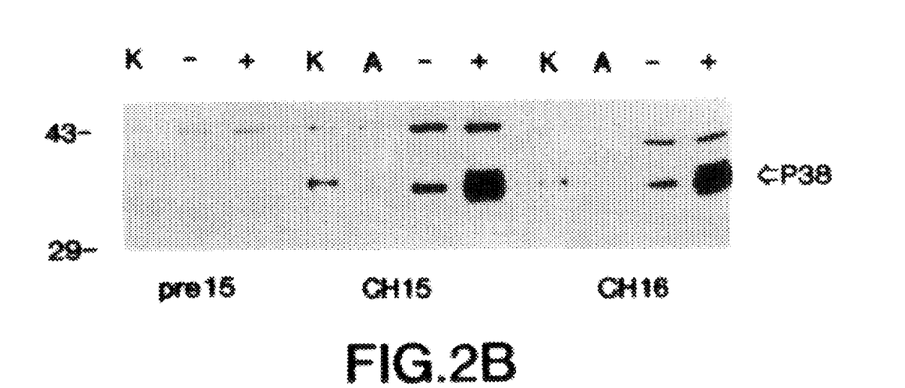

Both antisera specifically detected proteins of approximately 38-kDa (P38) in COS-1 cells transiently transfected with a construct expressing full-length CRKL (FIG. 2B, lanes +) and in K562 cells (FIG. 2B, lanes K). COS-1 cells also contained a substantial amount of endogenous P38 protein (FIG. 2B, lanes −). When the same blot was stripped and reacted with anti-phosphotyrosine (α-p-Tyr) monoclonal antibodies, bands of an apparently similar molecular mass were detected in K562, the CRKL-transfected COS-1 cells, and substantially weaker in A498 and untransfected COS-1 cells (not shown).

CRKL is phosphorylated on tyrosine by ABL and BCR/ABL

Figure 3A:
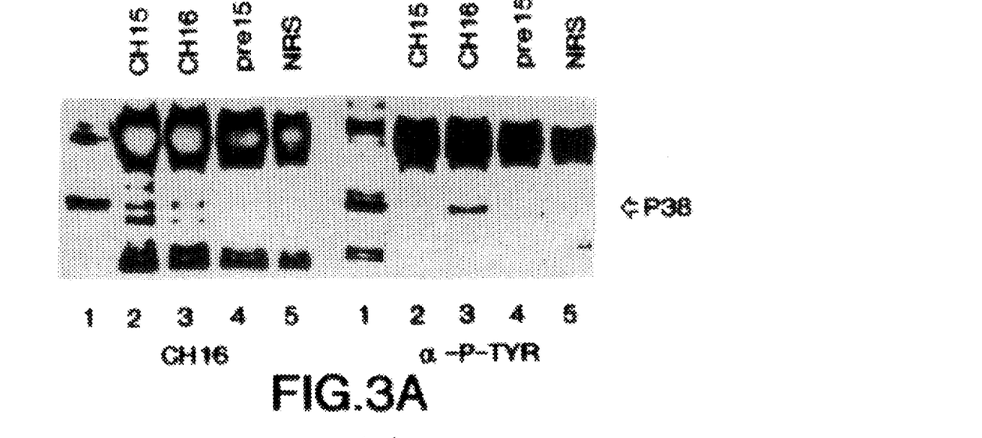

The protein of 38-kDa detected by the α-p-Tyr antibody was one of the most prominent p-Tyr containing proteins detected in that cell line. To confirm its identity, cellular extracts of K562 were incubated with CRKL antisera, and immunoprecipitates were run in duplicate. The Western blot reacted with CH16 antiserum showed specific immunoprecipitation of P38; the duplicate filter reacted with the α-p-Tyr monoclonal demonstrated that CRKL was indeed the prominent p-Tyr containing P38 in K562 (FIG. 3A).

Figure 3B:
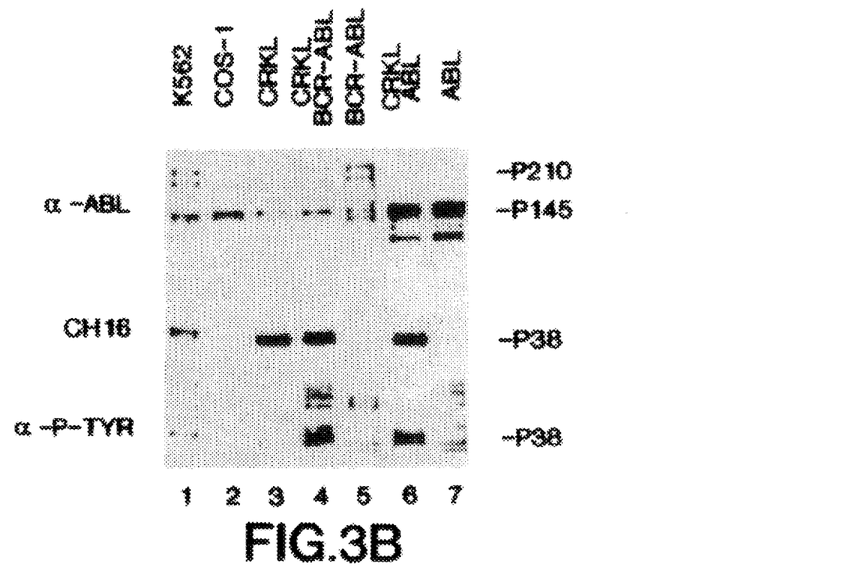

To investigate whether CRKL can act as a substrate for BCR/ABL, cotransfections of CRKL, BCR/ABL P210, BCR/ABL P190 and ABL into COS-1 cells were performed. The presence of P210 BCR/ABL, P145 ABL and P38 CRKL was confirmed using anti-ABL monoclonal antibodies and CH16 (FIG. 3B). Tyrosine-phosphorylated P38 was clearly visible in K562 (FIG. 3B lane 1), and in cells co-transfected with CRKL+BCR/ABL P210 (lane 4), with CRKL+BCR/ABL P190 (not shown) and with CRKL+ABL (lane 6) (also see FIG. 4).

Figure 3C:
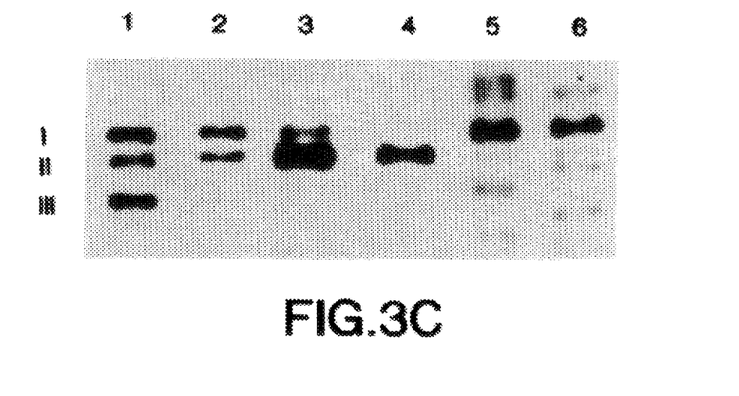

The phosphorylation of CRKL resulted in mobility shifts. On gels with higher resolution, the P38 band in K562 resolved into two closely migrating forms I and II detected by CH16 (FIG. 3C lane 2). CH15 detected forms I and II, and a third protein product, III (FIG. 3C lane 1). Form II was present in COS-1 cells transfected with CRKL, and form I appeared in cells co-transfected with CRKL+ABL (FIG. 3C lanes 4 and 3, respectively). Form I contained phosphotyrosine (FIG. 3C lanes 5 and 6). This suggests that I and II are differentially phosphorylated forms of one protein, CRKL.

p38 forms a specific complex with ABL and BCR/ABL

Figure 4A:
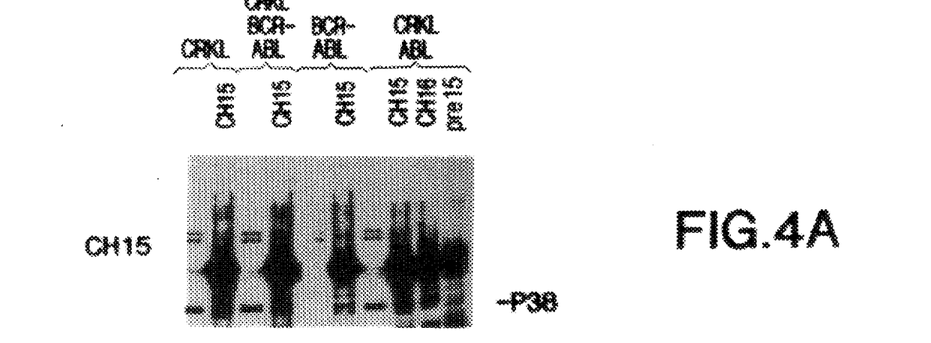
Figure 4B:
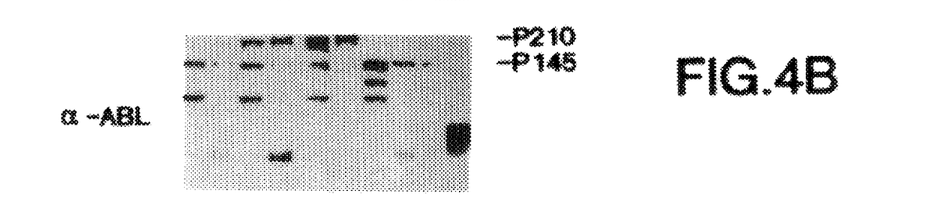
Figure 4C:
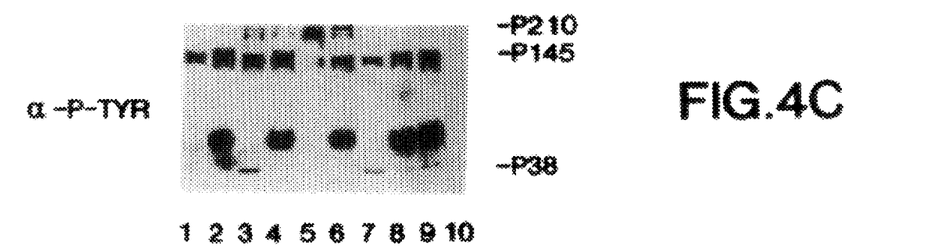

The phosphorylation of CRKL on tyrosine in BCR/ABL and ABL overexpressing cells suggested that they may interact directly. To confirm this we determined whether ABL and/or BCR/ABL were present in immune complexes of P38 with the CRKL antisera. CH15 and CH16 antisera did not react directly with either ABL or BCR/ABL (compare FIGS. 4A and 4B, lanes 3,5,7). CH15 immunoprecipitation followed by Western blot analysis with ABL antibodies showed ABL P145 to be present in immunoprecipitates of COS-1 cells expressing CRKL and CRKL+ABL (FIG. 4B lanes 2 and 8). CH16 antiserum also co-immunoprecipitated ABL P145 in cells expressing CRKL+ABL (FIG. 4B lane 9). Similarly, BCR/ABL P210 was recovered in CH15 and CH16 immunoprecipitates from BCR/ABL P210+CRKL and BCR/ABL P210 expressing cells (FIG. 4B lanes 4 and 6; results not shown). Anti-p-Tyr antibodies showed that P210, P145 and P38 present in the CH15 and CH16 immunoprecipitates are phosphorylated on tyrosine (FIG. 4C lanes 4,6,8,9). The identity of these proteins was confirmed by co-electrophoresis of the same extracts without prior immunoprecipitation (FIG. 4B lanes 1,3,5,7). Control preimmune serum did not precipitate CRKL or ABL (FIGS. 4A and 4B, lanes 10).

Figure 4D:
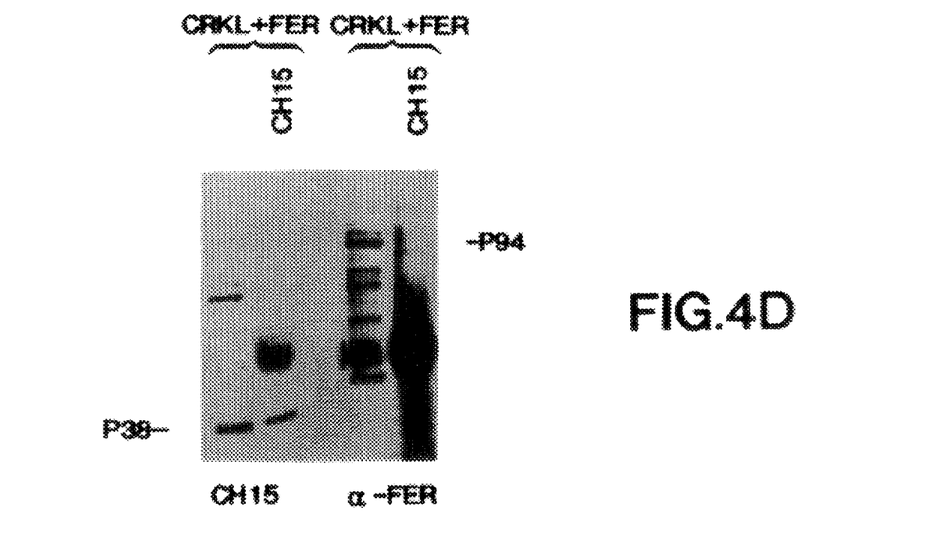

The interaction of CRKL with BCR/ABL and ABL appears to be specific. The non-receptor tyrosine kinase FER is related to ABL and, as ABL, is located both in the cytoplasm and in the nucleus (17,21,22). CH15 immunoprecipitates of COS-1 cells transfected with CRKL+FER did not contain detectable amounts of P94$^{fer}$ (FIG. 4D).

Identification of CRKL-binding proteins

Figure 5A:
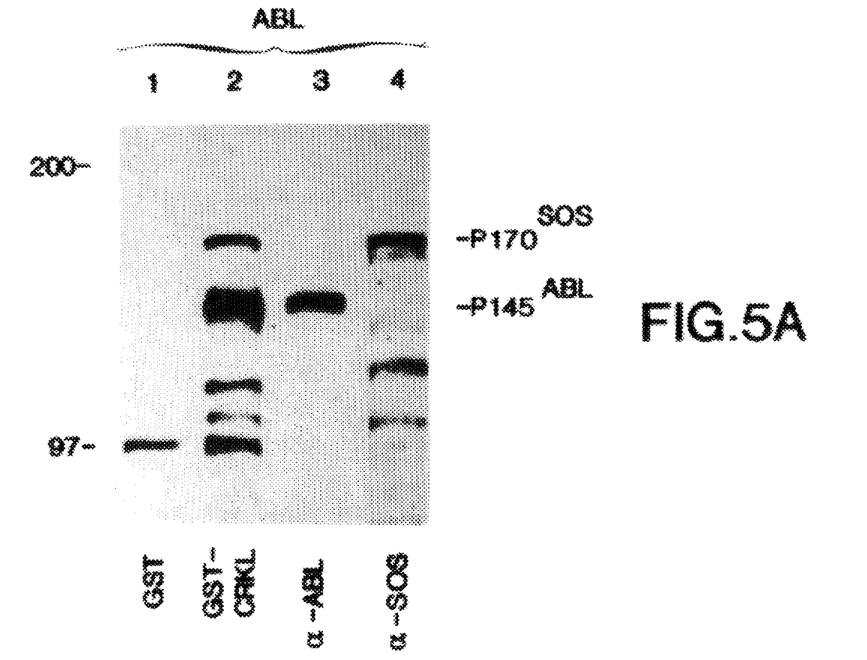
Figure 5B:
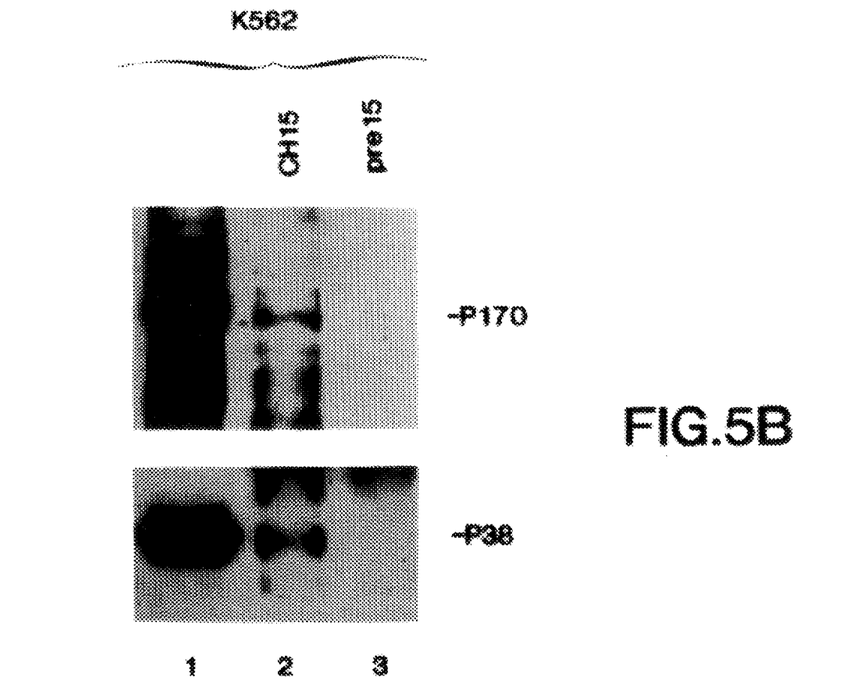

Total cellular extracts of ABL-expressing COS-1 cells were Western blotted and incubated with GST or GST-CRKL fusion proteins to examine the binding capability of CRKL to other proteins. GST alone bound very little protein (FIG. 5A lane 1), whereas GST-CRKL bound to 4 proteins larger than 100 kDa (FIG. 5A lane 2). The most prominent of these corresponded in migration to the overexpressed P145$^{abl}$ (FIG. 5A lane 3). In a similar experiment, GST-CRKL also bound to BCR/ABL P210 (not shown). A second protein showing a relatively strong reaction with GST-CRKL had a mobility similar to that of P170$^{SOS}$ detected on the same membrane by α-SOS antibodies (compare FIG. 5A lanes 2 and 4). The SH3 binding domain of nucleotide exchange factor mSOS1 has recently been shown to not only bind GRB2, but also the CRK SH3 domain in vitro (23). To verify a potential interaction of CRKL with mSOS1 in whole cells, cellular extracts of K562 were incubated with CH15 or control preimmune antiserum, Western blotted and probed with CH16 or α-SOS antibodies. A P170 protein immunoreactive with the α-SOS antibodies was present in the CH15 immunoprecipitate (FIG. 5B).

Our results demonstrate that CRKL binds to ABL and BCR/ABL in vivo. Interestingly, interactions between CRK and ABL have also been demonstrated (H. Hanafusa, pers. comm.). One of the consequences of binding of BCR/ABL or ABL and CRKL is the phosphorylation of CRKL on tyrosine. Since a small fraction of endogenous CRKL, without overexpression of ABL or BCR/ABL, also contains phosphotyrosine, we suggest that tyrosine phosphorylation of CRKL by ABL could be a normal cellular process.

Since BCR/ABL P210 retains the capability of ABL to complex with CRKL, it is plausible that in Ph-positive leukemia that the deregulated kinase activity of BCR/ABL causes excessive phosphorylation of CRKL on tyrosine. Significantly, in the BCR/ABL p210 expressing CML cell line K562 the majority of p38 CRKL was found to be tyrosine-phosphorylated. The presence of a prominent tyrosine-phosphorylated p36–p41 protein in K562 has also been shown by others using immunoblotting and anti-phosphotyrosine antibodies (24,25) This protein is phosphorylated on tyrosine specifically in CML cell lines but not in matched cell line controls (24). Our data strongly suggest that the p36–p41 identified by these investigators is CRKL.

A second possible mechanism of CRKL and CRK involvement in leukemia is through gene dosage. A duplication of the Ph chromosome is frequently seen in blast phase CML, and an i(17q), which involves a deletion of 17p and duplication of 17q is detected in around 20% of patients in acute phase of CML. Both abnormalities modify the gene copy number of either CRKL or CRK (26,27). In this context, K562 is an example of a CML cell line having an increased copy number and mRNA expression of CRKL over CRK.

Both GRB2 and CRKL interact with BCR/ABL, albeit apparently through a different mechanism: GRB2 binds BCR/ABL through the phosphorylated tyrosine residue Y$^{177}$ in the BCR part of the protein (10,11), while CRKL is likely to bind the ABL part of BCR/ABL. Both GRB2 (11,12) and CRKL (this study) are able to complex with mSOS1. Upon activation of receptor tyrosine kinases, GRB2/SOS complexes are recruited to the plasma membrane where RAS is located, thereby activating the RAS pathway. The deregulated BCR/ABL kinase also seems to activate the RAS pathway through GRB2/SOS (10,11). The present finding of association of CRKL with mSOS1 suggests that CRKL might also regulate the RAS pathway. Independent of this, it is clear that CRKL can bind to BCR/ABL and becomes phosphorylated on tyrosine as a result of this interaction.

EXAMPLE 2

Materials and Methods

Cells and patient samples

Cellular lysates of patients were prepared as described (46). Blood samples were obtained from patients as part of a program project study sponsored by the National Cancer Institute. All patients signed an appropriate Informed Consent Form. The ALL cell line sup-B15 and the BCR/ABL-negative myeloid cell line KG-1 have been described previously (47, 48). The CML cell line K562 was from the ATCC.

Antisera and Western blotting

The CRKL-specific CH16 antiserum was raised against a bacterially expressed CRKL-glutathione-S-transferase (GST) fusion protein containing the CRKL amino acid residues 184–247. This region, which is diverged between CRKL and CRK (ref 16), was inserted into pGEX-2T as Sau3A-EcoRI+EcoRI-RsaI. fragments. Bacterial cultures expressing the pGEX constructs were induced with 0.25 mM IPTG, and lysed by sonication. GST-CRKL fusion proteins were purified on glutathione-Sepharose columns and used to immunize rabbits. Anti-p-Tyr (Ab-2) monoclonal antibodies were from Oncogene Science, Inc. (OSI). The monoclonal anti-Abl antibody 8E9 has been described elsewhere (46).

Western blotting and detection of BCR/ABL P210 was as described previously (46). For detection of CRKL, lysates of 4×10$^6$ peripheral blood cells or 1×10$^6$ K562 cells were separated on 12% SDS-PAGE gels and transferred to Hybond-ECL (Amersham). Membranes were blocked overnight at 4° C. in TBST (20 mM Tris-HCl pH 8.0, 150 mM NaCl, 0.1% Tween) plus 5% non-fat milk (Biorad) and then incubated for 2 hours at room temperature with CH16 antiserum diluted 1:1000 in TBST+2% milk. Bound antibodies were detected with horseradish peroxidase labeled secondary antibodies (Biorad; 1:3000 in TBST +2% milk). Anti-p-Tyr immunoblots were blocked overnight at 4° C. in TBST+2% BSA+1% ovalbumin, and then incubated with the α-p-Tyr monoclonal antibodies at 1 µg/ml in TBST+1% fish gelatin+0.1% BSA. Blots were developed using the ECL reagents (Amersham) and exposed to Hyperfilm-ECL (Amersham).

Results

Figure 6:
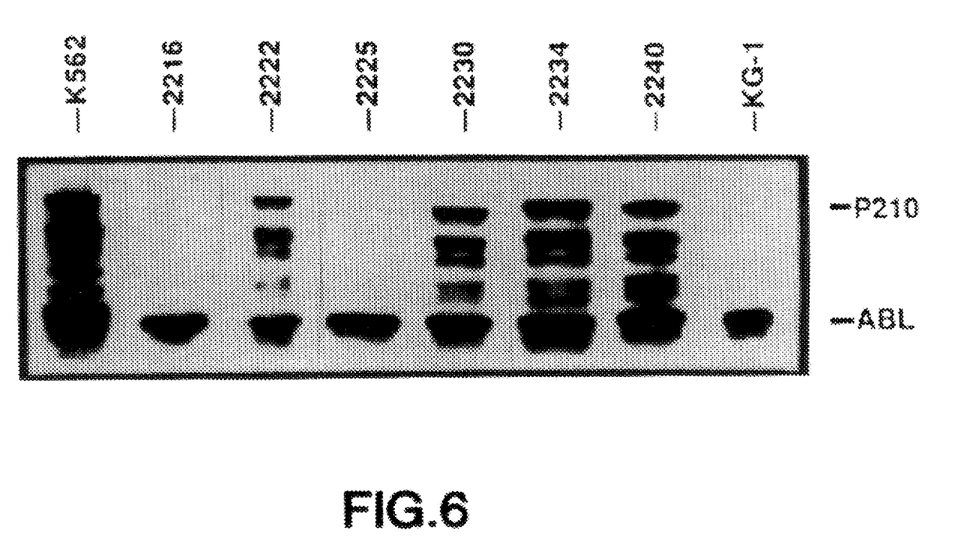
FIG. 6. Western blot analysis of P210 expression levels in CML patient samples. The identifying numbers of the samples are shown above the panel. Positive and negative controls include the cell line K562 and the human myeloid cell line KG-1, respectively. The blot was probed with α-ABL antibodies. The positions of BCR/ABL P210 and ABL P145 are indicated.

A Western blot analysis procedure has been previously developed to examine the presence of BCR/ABL in peripheral blood lymphocytes of patients. BCR/ABL P210 could easily be detected in the CML cell line K562 and in peripheral blood samples of CML patients (FIG. 6). Lower molecular weight proteins are usually also detected by the Abl antibodies and are likely to be degradation products of the P210 or may represent some altered form of the BCR/ABL protein (46). BCR/ABL was not detectable in the acute myelogenous leukemia cell line KG-1 or in samples of CML patients who had achieved remission (FIG. 6, samples 2216 and 2225).

Figure 7:
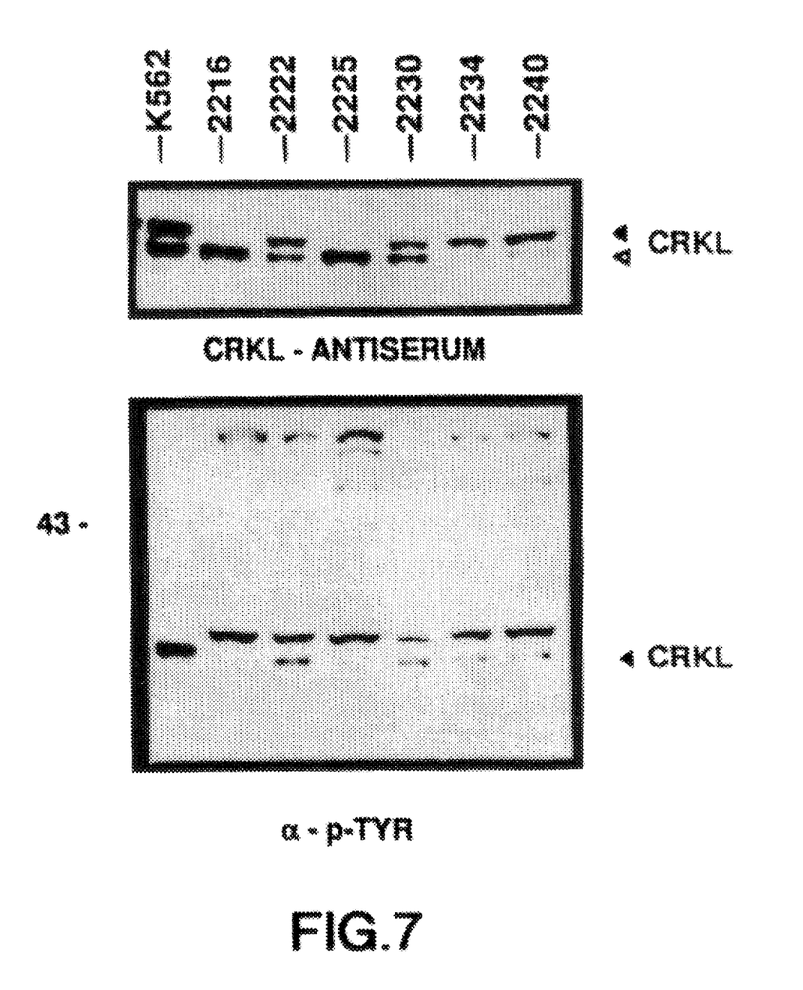
FIG. 7. CRKL is specifically tyrosine-phosphorylated in CML patient samples expressing P210. Upper panel: immunodetection of CRKL protein using CRKL antiserum CH16. The location of the CRKL proteins are indicated to the right. The open arrowhead indicates the nonphosphorylated form, the closed arrowhead the tyrosine-phosphorylated form. Lower panel: detection of tyrosine-phosphorylated CRKL using α-p-Tyr antibodies (OSI). The position of the 43 kDa marker is indicated to the left. The position of the phosphorylated form of CRKL is indicated to the right. Samples include the remission CML samples 2216 and 2225 and the chronic phase CML samples 2222, 2230, 2234 and 2240 (see also Table I).
Figure 8A:
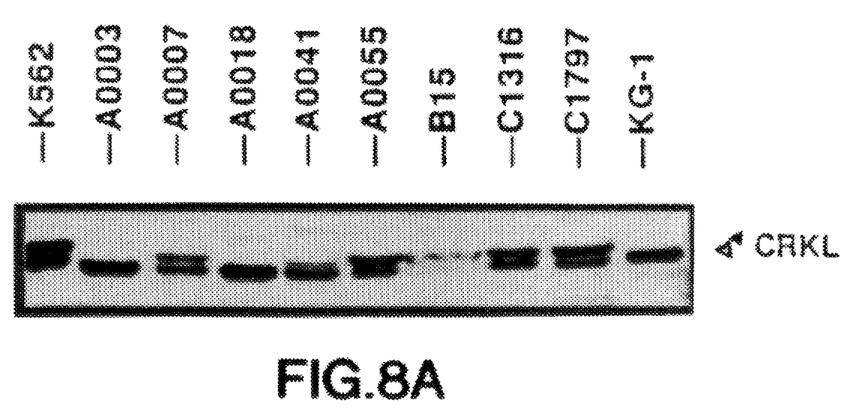

All the peripheral blood lymphocyte samples contained clearly detectable levels of P38 CRKL. The CRKL proteins migrated as a single band in the remission samples 2216 and 2225 (FIG. 7, upper panel) and in KG-1 (FIG. 8). However, two distinct but closely migrating CRKL bands were present in the cell line K562 and in the samples of CML patients in chronic phase (FIG. 7, upper panel) or in blast crisis (FIG. 8A, samples C1316 and C1797) that expressed the P210 BCR/ABL protein: part of the total amount of CRKL present in these samples had undergone a mobility shift.

Mobility shifts can be caused by secondary modifications and are well-known to occur as a consequence of phosphorylation. Probing of a duplicate Western blot with anti-phosphotyrosine ($\alpha$-p-Tyr) antibodies revealed that the more slowly migrating band present in the P210 expressing samples contained phosphotyrosine (FIG. 7, lower panel). All peripheral blood samples contained an additional tyrosine-phosphorylated protein in this size range. However, phosphorylation of this unidentified protein was constant and did not correlate with the presence of BCR/ABL.

Figure 8B:
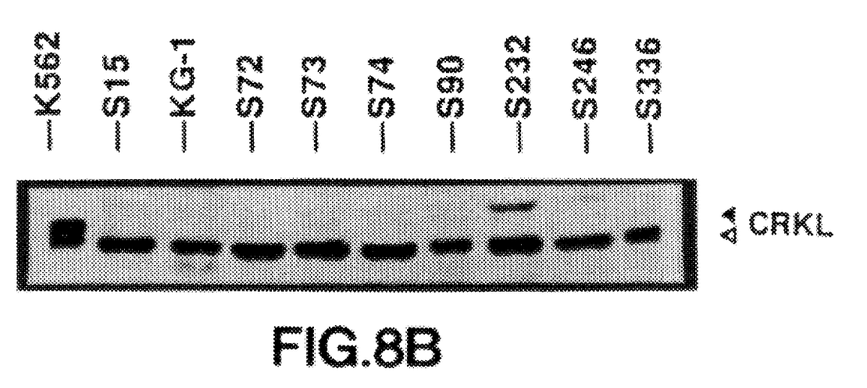

A percentage of Ph-positive ALL patients express P190, a BCR/ABL fusion protein containing only the BCR amino acids encoded by exon 1 but the same ABL moiety as P210 (ref 3, 29, 30). All of the P190-expressing ALL samples examined here showed the P38 doublet characteristic for the presence of phosphorylated and non-phosphorylated forms of CRKL (FIG. 8A, samples A0007, A0041, A0055 and B15; Table I). Indeed, the slower migrating form contained phosphotyrosine (not shown). In contrast, Ph-negative ALL patient samples contained only non-phosphorylated CRKL (FIG. 3A, samples A0003 and A0018; results not shown). Other Ph-negative samples examined included peripheral blood lymphocytes of a normal control and of patients with acute myeloid leukemia (AML), diffuse large cell lymphoma, myeloproliferative syndrome (MPS), Down's syndrome, chronic lymphocytic leukemia (CLL) and chronic myelomonocytic leukemia (CMML). None of these contained the tyrosine-phosphorylated form of CRKL (FIG. 8B; and data not shown).

When comparing the relative expression levels of BCR/ABL P210 or P190 and the degree of CRKL phosphorylation (as determined by the percentage of the CRKL proteins that had undergone a mobility shift) there seems to be a direct correlation between the level of BCR/ABL expression and the degree of CRKL phosphorylation (Table I).

TABLE I

Peripheral blood samples examined for CRKL phosphorylation

| sample | disease | phase | P210 | P190 | % P-Y-CRKL[1] |
|---|---|---|---|---|---|
| K562[2] | CML | blast | ++++ | − | 70 |
| 2216 | CML | remission | − | − | 0 |
| 2222 | CML | chronic | +++ | − | 60 |
| 2225 | CML | remission | − | − | 0 |
| 2230 | CML | chronic | +++ | − | 50 |
| 2234 | CML | chronic | ++++ | − | 90 |
| 2240 | CML | chronic | ++++ | − | 90 |
| 2107 | CML | chronic | ++++ | − | 50 |
| 2112 | CML | chronic | ++ | − | 20 |
| 2130 | CML | chronic | +++ | − | 40 |
| A0003 | ALL | | − | − | 0 |
| A0007 | ALL | | − | ++++ | 50 |
| A0018 | ALL | | − | − | 0 |
| A0041 | ALL | | − | ++ | 20 |
| A0055 | ALL | | − | ++++ | 70 |
| B15[2] | ALL | | − | ++++ | 60 |
| C1316 | CML | blast | ++++ | − | 50 |
| C1797 | CML | blast | ++++ | − | 70 |
| S15 | normal | | | | 0 |
| KG-1[2] | Acute Myeloid Leukemia | | | | 0 |
| S72 | Acute Myeloid Leukemia | | | | 0 |
| S73 | Diffuse Large Cell Lymphoma | | | | 0 |
| S74 | Diffuse Large Cell Lymphoma | | | | 0 |
| S90 | Myeloproliferative Syndrome | | | | 0 |
| S232 | Down's Syndrome | | | | 0 |
| S246 | Chronic Lymphocytic Leukemia | | | | 0 |
| S336 | Chronic Myelomonocytic Leukemia | | | | 0 |

[1] determined by visual comparison of the intensities of the two CRKL bands; approximately equal levels of total CRKL protein were present in the peripheral blood lymphocyte samples. The cell line K562 contained higher levels of total CRKL protein. Samples S15 through S336 do not contain BCR/ABL P210 or P190.
[2] cell lines The deregulated tyrosine kinase activity displayed by BCR/ABL has prompted a number of investigators to examine CML cell lines or P210-transfected cell lines for novel phosphotyrosine-containing proteins. In 1992, Freed and Hunter[29] reported a 41-kDa protein as one of the most prominent phosphotyrosine-containing proteins in the cell line K562. In addition, pp41 was found in two other CML cell lines and in Ph-positive B-cell lines established from CML patients, but not in Ph-negative B-cell lines established from the same patients. It was reported that since pp41 was such a prominent substrate in cells containing $P210^{BCR/ABL}$, phosphorylation of this particular protein might be relevant to the pathogenesis of CML (49). Without being bound by theory, our data is consistent with CRKL being CRKL is identical to pp41 since it is also the most prominent phosphotyrosine-containing protein detected by us in K562 and since BCR/ABL-dependent phosphorylation of CRKL fits the described profile of pp41 detection in Ph-positive and Ph-negative human hematopoietic cell lines (49).

We have found that P38 CRKL is expressed at clearly detectable levels in human peripheral blood cells and that CRKL is present in a non-tyrosine phosphorylated form in these cells. However, CRKL becomes phosphorylated on tyrosine in peripheral blood cells expressing BCR/ABL P210 or P190, and the level of CRKL phosphorylation was found to correlate well with the amount of BCR/ABL detected by Western blotting. This suggests that a single BCR/ABL molecule is capable of phosphorylating only a limited number of CRKL molecules or, alternatively, that CRKL and BCR/ABL form a relatively permanent or stable complex.

CRKL is capable of forming complexes with ABL and with BCR-ABL when coexpressed in COS-1 cells. In addition, bacterially expressed CRKL can bind both overexpressed ABL and BCR/ABL in a Western blot binding assay (45). Binding of CRKL to BCR/ABL is therefore likely to involve the ABL part of the molecule. In COS-1 cells CRKL can be phosphorylated by both ABL and BCR/ABL. Nonetheless, in peripheral blood cells CRKL is only phosphorylated to detectable levels by BCR/ABL and not by the relatively abundant ABL protein (see FIG. 6). We therefore conclude that the high degree of CRKL phosphorylation in Ph-positive cells can be considered abnormal.

CRKL is homologous to the adaptor protein CRK, also consisting exclusively of one SH2 and two SH3 domains (15, 28). In HeLa cells CRK appears to be present solely in the tyrosine-phosphorylated form, reportedly due to rapid post-translational modification (50). CRK is phosphorylated on tyrosine residue $Y^{221}$ by p145 ABL, and binds other CRK molecules in a phospho-tyrosine dependent manner. It has been proposed that tyrosine phosphorylated $Y^{221}$ becomes a binding site for the CRK SH2 domain, thereby allowing intramolecular binding. As a consequence, binding of ABL and other SH3 binding molecules would be abolished. Thus, in analogy to SRC, tyrosine-phosphorylation of CRK followed by intramolecular binding to its own SH2 domain would result in the generation of an "inactive" CRK molecule unable to participate in signaling (50).

From our results it is clear that in hematopoietic cells CRKL is only present in a non-phosphorylated form. Whether this form is unable to engage in other molecular interactions or whether the tyrosine-phosphorylated form is "inactive" remains to be determined. If phosphorylation of CRKL would induce the interaction with other cellular proteins, this could activate certain signal transduction pathways and potentially impair the further terminal differentiation of myeloid precursor cells. Alternatively, if tyrosine-phosphorylation would inactivate CRKL, expression of BCR/ABL will result in loss-of-function of CRKL, the degree of which is correlated with the amount of BCR/ABL present.

This postulated loss-of-function is not incompatible with the current views on the pathobiology of CML, which is characterized by an expansion of the most mature proliferating myeloid cell compartment (51). CML progenitor cells most likely undergo one or more additional divisions, show an increased lifespan and have longer transit times in the maturation compartments than do normal precursors (for a review, see 52). If the signal transduction pathway in which CRKL is involved conveys signals which will eventually lead to terminal differentiation, partial abrogation of CRKL function could slowly result in an expanding pool of myeloid precursors. Support for a possible role for CRKL in terminal differentiation comes from the finding that microinjection of the related CRK protein into the rat pheochromocytoma cell line PC12 induces neuronal differentiation (53). Although we currently are unable to distinguish between these alternative hypotheses of CRKL activation, both are amenable to experimental investigation. Regardless of the consequences of CRKL phosphorylation, the phosphorylation of CRKL is a clear hallmark of Ph-positive leukemia, which we disclose as being useful for diagnostic and therapeutic purposes.

REFERENCES

1. Sawyers, C. L., Denny, C. T. and Witte, O. N. Leukemia and the disruption of normal hematopoiesis. Cell 64: 337–350, 1991.
2. Kantarjian, H. M., Deisseroth, A., Kurzrock, R., Estrov, Z. and Talpaz, M. Chronic myelogenous leukemia: a concise update. Blood 82: 691–703, 1993.
3. Heisterkamp, N., Voncken, J-W., van Schaick, H., and Groffen, J. Ph-positive leukemia. In: I. R. Kirsch (ed.), The causes and consequences of chromosomal aberrations, pp. 359–376. CRC Press, Boca Raton, Fla., 1993.
4. Wang, J. Y. J. Abl tyrosine kinase in signal transduction and cell cycle regulation. Curr. Opin. Genet. Dev. 3: 35–43, 1993.
5. McWhirter, J., Galasso, D., Wang, J. Y. J. A coiled-coil oligomerization domain of Bcr is essential for the transforming function of the Bcr-Abl oncoproteins. Mol. Cell. Biol. 13: 7587–7595, 1993.
6. Ron, D., Zannini, M., Lewis, M., Wickner, R. B., Hunt, L. T., Graziani, G., Tronick, S. R., Aaronson, S. A. and Eva, A. A region of proto-dbl essential for its transforming activity shows sequence similarity to a yeast cell cycle gene, CDC24, and the human breakpoint cluster gene, bcr. The New Biologist 3: 372–379, 1991.
7. Diekmann, D., Brill, S., Garrett, M. D., Totty, N., Hsuan, J., Monfries, C., Hall, C., Lim, L., and Hall, A. Bcr encodes a GTPase-activating protein for $p21^{rac}$. Nature 351: 400–402, 1991.
8. Lowenstein, E. J., Daly, R. J., Batzer, A. G., Li, W., Margolis, B., Lammers, R., Ullrich, A., Skolnick, E. Y., Bar-Sagi, D. and Schlessinger, J. The SH2 and SH3 domain-containing protein GRB2 links receptor tyrosine kinases to ras signalling. Cell 70: 431–442, 1992.
9. McCormick, F. How receptors turn Ras on. Nature 363: 15–16.
10. Pendergast, A. M., Quilliam, L. A., Cripe, L. D., Bassing, C. H., Dai, Z., Li, N., Batzer, A., Rabun, K. M., Der, C. J., Schlessinger, J. and Gishizky, M. L. BCR-ABL-induced oncogenesis is mediated by direct interaction with the SH2 domain of the GRB-2 adaptor protein. Cell 75: 175–185, 1993.
11. Puil, L., Liu, J., Gish, G., Mbamalu, G., Bowtell, D., Pelicci, P. G., Arlinghaus, A., Pawson, T. Bcr-Abl oncoproteins bind directly to activators of the Ras signalling pathway. EMBO J. 13: 764–773, 1994.
12. Koch, C. A., Anderson, D., Moran, M. F., Ellis, C., Pawson, T. SH2 and SH3 domains: elements that control interactions of cytoplasmic signaling proteins. Science 252: 668–74, 1991.
13. Mayer, B. J., Hamaguchi, M. and Hanafusa, H. A novel viral oncogene with structural similarity to phospholipase C. Nature 332: 272–275, 1988.
14. Mayer, B. J. and Hanafusa, H. Mutagenic analysis of the v-crk oncogene: requirement for SH2 and SH3 domains and correlation between increased cellular phosphotyrosine and transformation. J. Virol. 64: 3581–3589, 1990.
15. Reichman, C. T., Mayer, B. J., Keshav, S. and Hanafusa, H. The product of the cellular crk gene consists primarily of SH2 and SH3 regions. Cell Growth Differ. 3: 451–460, 1992.
16. ten Hoeve, J., Morris, C., Heisterkamp, N., and Groffen, J. Isolation and chromosomal localization of CRKL, a human CRK-like gene. Oncogene 8: 2469–2474, 1993a.
17. Hao, Q-L., Heisterkamp, N., and Groffen, J. Isolation and sequence analysis of a novel human tyrosine kinase gene. Mol. Cell. Biol. 9: 1587–1593, 1989.
18. Okayama, H., and Berg, P. A cDNA cloning vector that permits expression of cDNA inserts in mammalian cells. Mol. Cell. Biol. 3: 280–289, 1983.
19. Chomczynski, P. and Sacchi, N. Single-step method of RNA isolation by acid guanidinium thiocyanate-phenol-chloroform extraction. Anal. Biochem. 162: 156–159, 1987.
20. Sambrook, J., Fritsch, E. F. and Maniatis, T. Molecular cloning: A laboratory manual. Second edition, Cold Spring Harbor Laboratory Press, Cold Spring Harbor, N.Y., 1989
21. Hao, Q-L., Ferris, D. K., White, G., Heisterkamp, N., and Groffen, J. Nuclear and cytoplasmic location of the FER tyrosine kinase. Mol. Cell. Biol. 11: 1180–1183, 1991.
22. Van Etten, R., Jackson, P. and Baltimore, D. The mouse type IV c-abl gene product is a nuclear protein, and activation of transforming ability is associated with cytoplasmic localization. Cell 58: 669–678, 1989.

23. Gout, I., Dhand, R., Hiles, I. D., Fry, M. J., Panayotou, G., Das, P., Truong, O., Totty, N. F., Hsuan, J., Booker, G. W., Campbell, I. D., Waterfield, M. D. The GTPase dynamin binds to and is activated by a subset of SH3 domains. Cell 75: 25–36, 1993.

24. Freed, E. and Hunter, T. A 41-kilodalton protein is a potential substrate for the p210$^{bcr-abl}$ protein-tyrosine kinase in chronic myelogenous leukemia cells. Mol. Cell. Biol. 12: 1312–1323, 1992.

25. Naldini, L., Stacchini, A., Cirillo, D. M., Aglietta, M., Gavosto, F., Comoglio, P. M. Phosphotyrosine antibodies identify the p210$^{c-abl}$ tyrosine kinase and proteins phosphorylated on tyrosine in human chronic myelogenous leukemia cells. Mol. Cell. Biol. 6: 1803–1811, 1986.

26. ten Hoeve, J., Morris, C., Poustka, A., Groffen, J. and Heisterkamp, N. Isolation of NotI sites from chromosome 22q11. Genomics 18: 588–597, 1993b.

27. Fioretos, T., Heisterkamp, N., Groffen, J., Benjes, S. and Morris, C. CRK proto-oncogene maps to human chromosome band 17p13. Oncogene 8: 2853–2855, 1993.

28. Matsuda M, Tanaka S, Nagata S, Kojima A, Kurata T, Shibuya M: Two species of human CRK cDNA encode proteins with distinct biological activities. Mol Cell Biol 12: 3482, 1992

29. Campbell ML, Arlinghaus RB: Current status of the BCR gene and its involvement with human leukemias. Adv Cancer Res 57: 227, 1991

30. Van Etten RA: The molecular pathogenesis of the Philadelphia-positive leukemias: implications for diagnosis and therapy, in Freireich EJ, Kantarjian H (eds): Leukemia: Advances Research and Treatment. The Netherlands, Kluwer Academic, 1993

31. Muller AJ, Young JC, Pendergast AM, Pondel M, Landau NR, Littman DR, Witte ON: BCR first exon sequences specifically activate BCR/ABL tyrosine kinase oncogene of Philadelphia chromosome-positive human leukemias. Mol Cell Biol 11: 1785, 1991

32. McWhirter JR, Wang JYJ: Activation of tyrosine kinase and microfilament-binding functions of c-abl by bcr sequences in bcr/abl fusion proteins. Mol Cell Biol 11: 1553, 1991

33. Daley GQ, van Etten RA, Baltimore, D: Induction of chronic myelogenous leukemia in mice by the P210 BCR/ABL gene of the Philadelphia chromosome. Science 247: 824, 1990

34. Elefanty AG, Hariharan IK, Cory S: bcr-abl, the hallmark of chronic myeloid leukaemia in man, induces multiple haemopoietic neoplasms in mice. EMBO J 9: 1069, 1990

35. Heisterkamp N, Jenster G, ten Hoeve J, Zovich D, Pattengale P, Groffen J: Acute leukemia in BCR/AB$_L$ transgenic mice. Nature 344: 251, 1990

36. Li W, Kloetzer WS, Arlinghaus RB: A novel 53 kDa protein complexed with P210$^{bcr-abl}$ in human chronic myelogenous leukemia cells. Oncogene 2: 559, 1988

37. Campbell ML, Li W, Arlinghaus RB: P210 BCR/ABL is complexed to P160 BCR and ph-P53 proteins in K562 cells. Oncogene 5: 773, 1990

38. Liu J, Campbell M, Guo JQ, Lu D, Xian YM, Andersson BS, Arlinghaus R: BCR-ABL tyrosine kinase is autophosphorylated or transphosphorylates P160 BCR on tyrosine predominantly within the first BCR exon. Oncogene 8: 101, 1993

39. Lu D, Liu J, Campbell M, Guo JG, Heisterkamp N, Groffen J, Canaani E, Arlinghaus R: Tyrosine phosphorylation of P160 BCR by P210 BCR-ABL. Blood 82: 1257, 1993

40. Druker B, Okuda K, Matulonis U, Salgia R, Roberts T, Griffin JD. Tyrosine phosphorylation of rasGAP and associated proteins in chronic myelogenous leukemia cell lines. Blood 79: 2215, 1992

41. Matsuguchi T, Salgia R, Hallek M, Eder M, Druker B, Ernst TJ, Griffin JD: Shc phosphorylation in myeloid cells is regulated by granulocyte macrophage colony-stimulating factor, interleukin-3, and steel factor and is constitutively increased by p210$^{BCR/ABL}$. J Biol Chem 7: 5016, 1994

42. Tauci T, Boswell HS, Leibowitz D, Broxmeyer HE: Coupling between p210bcr/abl and Shc and Grb2 adaptor proteins in hematopoietic cells permits growth factor-independent link to Ras activation pathway. J Exp Med 179: 167, 1994

43. Mandanas RA, Leibowitz DS, Gharehbaghi K, Tauchi T, Burgess GS, Miyazawa K, Jayaram HN, Boswell HS: Role of p21 RAS in p210 bcr-abl transformation of murine myeloid cells. Blood 82: 1838, 1993.

44. Ernst TJ, Slattery KE, Griffin JD: p210$^{Bcr/Abl}$ and p160$^{v-Abl}$ induce an increase in the tyrosine phosphorylation of p93$^{c-Fes}$. J Biol Chem 269: 5764, 1994

45. ten Hoeve J, Kaartinen V, Fioretos T, Haataja L, Voncken J-W, Heisterkamp N, Groffen J: Cellular interactions of CRKL, an SH2-SH3 adaptor protein. Cancer Res: in press, 1994

46. Guo JQ, Wang JYJ, Arlinghaus RB: Detection of BCR-ABL proteins in blood cells of benign phase chronic myelogenous leukemia patients. Cancer Res 51: 3048, 1991

47. Koeffler HP, Golde DW: Acute myelogenous leukemia: A human cell line responsive to colony-stimulating activity. Science 200: 1153, 1978

48. Naumovski I, Morgan R, Hecht F, Link MP, Glader BE, Smith SD: Philadelphia chromosome-positive acute lymphoblastic leukemia cell lines without classical breakpoint cluster region rearrangement. Cancer Res 48: 2876, 1988

49. Freed E, Hunter T: A 41-kilodalton protein is a potential substrate for the p210$^{bcr-abl}$ protein-tyrosine kinase in chronic myelogenous leukemia cells. Mol Cell Biol 12: 1312, 1992

50. Feller SM, Knudsen B, Hanafusa H: c-Abl kinase regulates the protein binding activity of c-crk. EMBO J: in the press, 1994

51. Strife A, Clarkson B: Biology of chronic myelogenous leukemia: is discordant maturation the primary defect? Semin Hematol 25: 1, 1988

52. Clarkson B, Strife A: Linkage of proliferative and maturational abnormalities in chronic myelogenous leukemia and relevance to treatment. Leukemia 7: 1683, 1993

53. Tanaka S, Hattori S, Kurata T, Nagashima K, Fukui Y, Nakamura S, Matsuda M: Both the SH2 and SH3 domains of human CRK protein are required for neuronal differentiation of PC12 cells. Mol Cell Biol 13: 4409, 1993

Modifications of the above described modes for carrying out the invention that are obvious to those of skill in the fields of genetic engineering, protein chemistry, medicine, and related fields are intended to be within the scope of the following claims.

Every reference cited hereinbefore is hereby incorporated by reference in its entirety.

What is claimed is:

1. A method of diagnosing cancers arising from cells which express tyrosine phosphorylated CRKL protein, said method comprising a) obtaining a sample of cells suspected of expressing tyrosine phosphorylated CRKL protein;

b) determining the percent increase in tyrosine phosphorylated CRKL protein relative to normal control cells wherein an increase in the expression of phosphorylated CRKL protein relative to controls is associated with the presence of cancer.

2. The method according to claim 1 wherein the cancers which may be diagnosed arise from cells which comprise the Philadelphia chromosome.

3. The method according to claim 2 wherein the cancers are chronic myelogenous leukemia (CML) and acute lymphoblastic leukemia (ALL).

4. The method according to claim 1 wherein the expression of phosphorylated CRKL protein is detected immunologically.

5. The method according to claim 4 wherein the phosphorylated CRKL protein is detected with an antiphosphotyrosine antibody.

6. The method according to claim 4 wherein CRKL protein is detected as a doublet on a Western blot and the more slowly migrating band is the phosphorylated CRKL protein.

7. The method according to claim 6 wherein the cancers which are diagnosed are chronic myelogenous leukemia (CML) and acute lymphoblastic leukemia (ALL).

8. The method according to claim 4 wherein the expression of phosphorylated CRKL protein is detected using a colorimetric or radioimmunoassay.

9. A kit for diagnosing cancers arising from cells which express tyrosine phosphorylated CRKL protein, said kit comprising a) reagent capable of specifically binding to tyrosine phosphorylated CRKL protein which reagent is capable of being detected directly or indirectly;

b) instructions for using said reagent in an assay to detect the presence of tyrosine phosphorylated CRKL protein;

c) buffer reagents and reaction vessels to accomplish said assay; and d) a control reagent comprising CRKL protein obtained from non-neoplastic cells and which control reagent is used as a reference for determining the percent increase of tyrosine phosphorylated CRKL protein.

10. The kit according to claim 9 wherein said reagent capable of specifically binding to tyrosine phosphorylated CRKL protein comprises an antibody.

11. The kit according to claim 10 further comprising a second antibody capable of detecting the antibody capable of specifically binding to tyrosine phosphorylated CRKL protein.

12. The kit according to claim 10 wherein said second antibody is labelled with an enzyme, a radioisotope or a fluorescent moiety.

13. The kit according to claim 12 wherein the enzyme is horseradish peroxidase.

14. A kit for diagnosing cancers arising from cells which express tyrosine phosphorylated CRKL protein, said kit comprising a) a reagent capable of specifically binding to non-phosphorylated CRKL protein and tyrosine phosphorylated CRKL protein, which reagent is capable of being detected directly or indirectly;

b) optionally comprising an additional reagent which is capable of detecting only the phosphotyrosine residue on phosphorylated CRKL; and c) instructions for using said reagent or reagents in an assay to detect the presence of tyrosine phosphorylated CRKL protein.

15. The kit according to claim 14 further comprising buffer reagents and reaction vessels to accomplish said assay.

16. The kit according to claim 15 further comprising a control reagent comprising CRKL protein obtained from non-neoplastic cells and which control reagent is used as a reference for determining the percent increase of tyrosine phosphorylated CRKL protein.

17. The kit according to claim 16 wherein said reagent capable of specifically binding to CRKL protein comprises an antibody.

18. The kit according to claim 17 further comprising a second antibody capable of detecting the antibody capable of specifically binding to CRKL protein.

19. The kit according to claim 17 wherein said second antibody is labelled with an enzyme, a radioisotope or a fluorescent moiety.

20. The kit according to claim 19 wherein the enzyme is horseradish peroxidase.

* * * * *